(12) United States Patent
Shi et al.

(10) Patent No.: US 11,376,595 B2
(45) Date of Patent: Jul. 5, 2022

(54) DROPLET DIGITAL PCR CHIP (71) Applicant: Pilot Gene Technologies (Hangzhou) Co., Ltd., Hangzhou (CN)

(72) Inventors: Jian Shi, Hangzhou (CN); Shuanghong Xiang, Hangzhou (CN); Xiaohui Song, Hangzhou (CN)

(73) Assignee: Pilot Gene Technologies (Hangzhou) Co., Ltd., Hangzhou (CN)

( * ) Notice: Subject to any disclaimer, the term of this patent is extended or adjusted under 35 U.S.C. 154(b) by 256 days.

(21) Appl. No.: 16/465,438

(22) PCT Filed: Nov. 30, 2017

(86) PCT No.: PCT/CN2017/113847
§ 371 (c)(1),
(2) Date: May 30, 2019

(87) PCT Pub. No.: WO2018/099420
PCT Pub. Date: Jun. 7, 2018

(65) Prior Publication Data
US 2020/0001301 A1 Jan. 2, 2020

(30) Foreign Application Priority Data

Nov. 30, 2016 (CN) .......................... 201611088461.4
Dec. 30, 2016 (CN) .......................... 201611263102.8
Dec. 30, 2016 (CN) .......................... 201611265154.9

(51) Int. Cl.
*B01L 3/00* (2006.01)
*C12Q 1/686* (2018.01)
(52) U.S. Cl.
CPC ... *B01L 3/502784* (2013.01); *B01L 3/502715* (2013.01); *C12Q 1/686* (2013.01);
(Continued)

(58) Field of Classification Search
None
See application file for complete search history.

(56) References Cited

U.S. PATENT DOCUMENTS

| 2005/0272169 | A1* | 12/2005 | Griffin | ............. | B01L 3/502738 |
| | | | | | 436/514 |
| 2013/0078164 | A1* | 3/2013 | Baroud | ................. | B01L 3/0241 |
| | | | | | 422/502 |
| 2013/0217103 | A1* | 8/2013 | Bauer | ............... | B01L 3/502715 |
| | | | | | 435/287.2 |
| 2014/0065631 | A1 | 3/2014 | Froehlich et al. | | |

(Continued)

FOREIGN PATENT DOCUMENTS

| CN | 103343092 A | 10/2013 |
| CN | 105452873 A | 3/2016 |

(Continued)

OTHER PUBLICATIONS

"International Application No. PCT/CN2017/113847, International Search Report and Written Opinion dated Feb. 22, 3018", (dated Feb. 22, 2018), 17 pgs.

*Primary Examiner* — Matthew D Krcha
(74) *Attorney, Agent, or Firm* — Schwegman Lundberg & Woessner, P.A.

(57) ABSTRACT

The present invention discloses a droplet digital PCR chip. The droplet digital PCR chip includes at least one chip unit, each chip unit includes a chip body formed by bonding a top piece and a bottom piece, the chip body is internally provided with an inlet chamber, a droplet storage chamber, and an injection hole. The injection hole connects with the inlet chamber, a plurality of droplet generating channels are disposed between the inlet chamber and the droplet storage chamber, a height of the droplet generating channel is smaller than a height of the droplet storage chamber, an injection fluid is injected into the inlet chamber through the injection hole, and the injection fluid is emulsified and enters (Continued)

the droplet storage chamber at a junction of the droplet generating channels and the droplet storage chamber.

13 Claims, 6 Drawing Sheets

Specification includes a Sequence Listing.

(52) U.S. Cl.
CPC ..... *B01L 2200/10* (2013.01); *B01L 2300/042* (2013.01); *B01L 2300/048* (2013.01); *B01L 2300/0816* (2013.01); *B01L 2300/0819* (2013.01); *B01L 2300/0858* (2013.01); *C12Q 2565/619* (2013.01); *C12Q 2565/629* (2013.01)

(56) References Cited

U.S. PATENT DOCUMENTS

| | | | |
|---|---|---|---|
| 2015/0267246 A1* | 9/2015 | Baroud | B01L 3/502761 506/9 |
| 2016/0051958 A1 | 2/2016 | Kung et al. | |
| 2017/0022538 A1 | 1/2017 | Abate et al. | |

FOREIGN PATENT DOCUMENTS

| | | |
|---|---|---|
| CN | 105802843 A | 7/2016 |
| CN | 106754341 A | 5/2017 |
| CN | 106854618 A | 6/2017 |
| WO | WO-2016126865 A1 | 8/2016 |
| WO | WO-2018099420 A1 | 6/2018 |

* cited by examiner

DROPLET DIGITAL PCR CHIP

PRIORITY CLAIM TO RELATED APPLICATIONS

This application is a U.S. national stage filing under 35 U.S.C. § 371 from International Application No. PCT/CN2017/113847, filed on 30 Nov. 2017, and published as WO2018/099420 on 7 Jun. 2018, which claims the benefit under 35 U.S.C. 119 to Chinese Application No. 201611088461.4, filed on 30 Nov. 2016, and to Chinese Application No. 201611263102.8, filed on 30 Dec. 2016, and to Chinese Application No. 201611265154.9, filed on 30 Dec. 2016, the benefit of priority of each of which is claimed herein, and which applications and publication are hereby incorporated herein by reference in their entirety.

BACKGROUND OF THE INVENTION

Field of the Invention

The invention relates to a technical field of biochip, in particular to a droplet digital PCR chip.

Description of the Related Art

Fluorescent Quantitative Polymerase Chain Reaction (qPCR) has developed into a key routine technology in the field of molecular biology, and has greatly promoted the development of various research fields in life sciences. However, the PCR amplification efficiency are affected by many factors. It is difficult to ensure the same amplification efficiency between the standard samples and the actual samples from different batches or from various sources. Thus, the cycle threshold (Ct) value which is the basis of quantitative analysis, is not constant. Therefore, qPCR is mainly used for relative quantification, and its accuracy and reproducibility still cannot meet the requirements of quantitative analysis of molecular biology. In addition, due to the inhibition of PCR products to the enzyme-catalyzed reaction, the current gene mutation detection methods based on qPCR is often incapable of detecting low-abundance gene variation in somatic cells.

Digital PCR (dPCR) is an absolute nucleic acid quantification method based on single-molecule PCR. By utilizing microfluidic technology or other droplet generation methods, a large amount of diluted nucleic acid solution is dispersed into micro-wells or droplets. Ideally, the number of target nucleic acid per micro-well or per droplet is less than or equal to one. After amplification, the reactor with the target nucleic acid molecule gives a positive fluorescent signal, and the reactor without the target template shows negative fluorescent signal. Based on the relative ratio and the volume of the reactors, the nucleic acid concentration of the original solution can be derived. Unlike traditional quantitative PCR, digital PCR can achieve absolute quantification of the starting DNA template by direct counting numbers and Poisson correction analysis.

In addition, digital PCR is able to identify trace amount of mutant DNA in a large number of wild-type DNA backgrounds. Digital PCR separates the template DNA molecules into each micro-reactor, which can avoid the amplification inhibition of high-abundance wild-type allele to mutant allele, thereby improving the detection sensitivity of low-abundance mutant. Whereas sequencing and qPCR can barely detect mutations with abundance less than 1%, droplet digital PCR can detect as low as 0.001%, improving the sensitivity of mutation detection by a factor of 1000.

The traditional digital PCR involves a complicated process. In general, the sample is first manually diluted and dispersed into microplates, and then the microplates are placed on a thermal cycler for PCR reaction. After the reaction, the fluorescent signals in each microreactor are measured. The concentration or copy number of targets can be calculated using specific software according to the Poisson distribution and the ratio of the positive microreactors. The tedious steps, low throughput and low efficiency, as well as the lower detection accuracy and measurable dynamic range due to the limited number of microreactors, greatly limit the application of the traditional digital PCR.

In recent years, the development of microfluidic technology discloses new tools to the development of digital PCR. With the advantages in microfluidic manipulation, microfluidic technology allows us to disperse sample into nano-liters or even picolitres, and to create more micro-reactors than traditional methods, thus greatly improving the detection sensitivity, reliability and dynamic range of digital PCR. Furthermore, the advantages of microfluidic technology in automation, easy integration, and high throughput can also greatly improve the detection efficiency of digital PCR. Recently, several research groups and companies have developed digital PCR systems based on microfluidic technology, such as the microchamber-based BioMark™ system from Fluidigm and the droplet-based QX100™ system from Bio-Rad.

Micro-droplet technology refers to the formation of relatively stable and independent water-in-oil or oil-in-water microdroplets using immiscible phases. Among many different emulsification methods, droplet generation technologies based on microfluidic chips has been rapidly developed in recent years, and are widely used in the biological and material researches. The main principle is that when the two-phase liquid flows are pressed against each other at a specific angle, one of the continuous liquid streams breaks to form droplets. 'T-junction' and 'Flow focusing' are the two most common used structures for production of homogeneous droplets. The methods require an overall complex equipment system and a highly demanding fluid control system.

BRIEF SUMMARY OF THE INVENTION

The present invention discloses a droplet digital PCR chip, which can be used for rapid preparation of a large number of homogeneous droplets laying in the chip. Instead of performing single-droplet-detections using flow-cytometer-like equipment, the chip can be imaged and analyzed as a whole.

The droplet digital PCR chip includes at least one chip unit, each chip unit includes a chip body formed by bonding a top piece and a bottom piece, the chip body is internally provided with an inlet chamber, a droplet storage chamber, and an injection hole. The injection hole connects with the inlet chamber, a plurality of droplet generating channels are disposed between the inlet chamber and the droplet storage chamber, a height of the droplet generating channel is smaller than a height of the droplet storage chamber, an injection fluid is injected into the inlet chamber through the injection hole, and the injection fluid is emulsified and enters the droplet storage chamber at a junction of the droplet generating channels and the droplet storage chamber.

The present invention has a terrace structure at a junction of the droplet generating channel and the droplet storage chamber. The injection fluid is emulsified while passing through the terrace structure.

When using, the oil phase is firstly injected into inner chambers of the chip through the injection hole. After the chip is filled with the oil phase and all bubbles are expelled from the inner chambers, the aqueous phase is injected into the inlet chamber through the injection hole under a certain pressure, and then the aqueous phase enters the droplet storage chamber through the droplet generating channels. A terrace is formed at the junction of the droplet generating channel and the droplet storage chamber as the height of droplet generating channel is smaller than the height of droplet storage chamber. As a flow rate is accelerated by a surface tension, when the aqueous phase enters a relatively wide droplet storage chamber from the relatively narrow droplet generating channel, the aqueous phase partially enters the droplet storage chamber breaks with the aqueous phase in the droplet generating channel, forming droplets. This method can continuously generate droplets by using a single driving source. A size of the droplets is mainly determined by a surface tension and the configuration of the microstructure, and is less affected by the flow rate. A large number of droplets are finally laid in the droplet storage chamber. After the droplets are generated, the chip can be directly put into a thermal cycler for a PCR amplification. After the amplification, the chip can be placed into an analysis instrument for imaging and reading fluorescent signals.

According to one embodiment, the chip body may be further provided with an oil outlet hole and an oil outlet chamber, and the oil outlet chamber may be connected to the droplet storage chamber through a plurality of oil outlet channels. When generated droplets enter the droplet storage chamber, the corresponding volume of the oil phase may be drained to the oil outlet chamber through the oil outlet channels, and may be eventually drained through the oil outlet hole that connects with the oil outlet chamber. Said oil outlet channels are small enough that no droplets can pass through.

According to one embodiment, the oil outlet chamber may be disposed on an outer side of the droplet storage chamber.

According to one embodiment, the chip body may further be provided with a bubble storage groove that connects with the droplet storage chamber through at least one bubble channel.

Said bubble storage groove may be mainly used for storing of the bubbles in the droplet storage chamber. There may be no special requirement for the position and structure thereof. Considering the layout and rational utilization of the whole chip, the bubble storage groove can be place in the corner space, not the main area, of the chip as much as possible.

According to one embodiment, a bubble storage groove and the corresponding bubble channels are provided at the end of the inlet chamber.

According to one embodiment, an injection flow channel may be disposed between the injection hole and the inlet chamber. Said injection flow channel extends the time of injection fluid flowing from the injection hole to the inlet chamber, and equilibrates the pressure of injection fluid flowing to the droplet generating channels.

Said injection flow channel can be in various forms. In order to ensure the pressure equilibrium of injection fluid when flowing to droplet generating channels and to increase the stability of the droplet generation, said injection flow channel can be as long and tortuous as possible.

According to one embodiment, the droplet generating channels between the inlet chamber and the droplet storage chamber are unequal spaced according to the flow pressure changes in the flow channel. The intervals between droplet generating channels are big near the inlet hole, and gradually decreases as the inlet chamber extends into the droplet storage chamber.

The intervals between the droplet generating channels varies according to the flow pressure changes in the flow channel. The intervals between droplet generating channels are big near the inlet hole, and gradually decreases as the inlet chamber extends into the droplet storage chamber, so that the pressure in each droplet generating channel may be basically consistent which can ensure the homogeneous of generated droplets in the chip.

The droplet storage chamber may have various shapes, including, but not limited to U shapes, square shapes, and circular shapes and so on. The inlet chamber can be linear or curvilinear structure.

According to one of the embodiments, an elongated inlet chamber extends into the droplet storage chamber and turns the latter into a U shape. A plurality of droplet generating channels are parallelly disposed between the inlet chamber and both arms of the U-shaped droplet storage chambers. Increased number of droplet generating channels along the elongated inlet channels can greatly improve the throughput of droplet generation. Meanwhile, all the boundaries of the droplet storage chamber are not too far from the inlet channel, avoiding the droplets migrate over long distances and break.

An end of the inlet chamber near the injection hole may be defined as injection end. An elongated connecting channel may be disposed between the injection end and the injection hole.

Preferably, the droplet generating channel has circular chamfer at the end that connect with the droplet storage chamber, which can facilitate the generation and movement of droplets.

Further preferably, the circular chamfer has a length ranging from 1 μm to 500 μm in the droplet formation direction. The length of said circular chamfer affects the size of the generated droplets. Within a certain range, the droplet size increases as the length increases.

Preferably, the droplet generating channel has a rectangular cross section, with a width ranging from 10 μm to 500 μm, and a height ranging from 1 μm to 400 μm. The height of the droplet storage chamber may be ranging from 2 μm to 1000 μm. The size of the droplets may be directly related to the size of the droplet generating channels, the larger the width and height of the droplet generating channels, the larger the droplets. So, the size of the droplet generating channel needs to be within a reasonable range.

Further preferably, the width of the droplet generating channel increases near the end that connects with the droplet storage chamber and forms a bell mouth structure, which facilitates the generation and movement of droplets.

Preferably, the injection hole may be provided with a silicone sealing plug, this plug may be provided with a through hole that connects with the inlet chamber. Due to the good elasticity of silicone material, the pipette can be tightly matched with the sealing plug, which ensures, during the loading of oil phase or aqueous phase, the airtightness of the chip channels, a stable flow rate and pressure, and generation of homogeneous droplets.

The droplets prepared by the chip can be laid in a single, a double, or a multi-layer array in the droplet storage chamber. The droplets can remain stable and homogenous after a series of reactions such as PCR amplification, and analysis such as fluorescent signal acquisition can be performed after reaction.

According to one embodiment, a plurality of chip units are parallelly disposed in one droplet digital PCR chip. Integrating multiple chip units on one single chip can increase the reaction throughput and facilitate the multiple samples experiment.

Different openings or windows can be disposed on the chip to facilitate coordinating with various devices.

According to one embodiment, a vent hole may be disposed on the chip, which facilitates the elimination of air in the chip, and maintains the stable pressure level inside the chip. A window for detecting all droplets may be disposed on the chip, which may be useful for monitoring the reaction process and detecting the reaction results.

The bonding of the top and bottom pieces of the chip may be performed by thermal compression bonding, or other bonding methods such as jig or riveting.

Different materials can be used for the top and bottom pieces, including, but not limited to glass, PMMA (Polymethyl Methacrylate), PC (Polycarbonates), COC (Cyclic Olefin Copolymer), COP (Cyclic Olefin Polymers), PS (Polystyrene), etc.

According to one embodiment, the top and bottom pieces are transparent and dark respectively, which are beneficial for various inspections.

The transparent top piece facilitates various optical inspections, whereas the dark bottom piece increases the contrast between the fluorescent signals and the background, which is also beneficial for various detections.

In this invention, the height of the droplet generating channels in said digital PCR chip may be smaller than the droplet storage chamber, which forms a terrace at the junction of the droplet generating channel and the droplet storage chamber. When aqueous phase partially enters the relatively wide droplet storage chamber through a relatively narrow droplet generating channel, it accelerates due to the surface tension changes and breaks from the aqueous phase in the droplet generating channel to form droplets. The droplets can stably and evenly lay in the droplet storage chamber in the chip, and can be directly tested and detected without extra transfer operation, thereby greatly reduces the operation steps and simplifies the operating system. Moreover, the homogeneous droplets are generated at high speed and high throughput, which greatly shortens the time for droplet preparation.

Further, the chip may be provided with an oil outlet chamber. It can be used to maintain the pressure inside the chip within a specific range, which is favorable for equilibrating the internal flow pressure and stabilizing the pressure during the droplet generation process, so that the droplets can be stable during the generation and the subsequent PCR reaction.

Further, the chip may be provided with a bubble storage groove, so that a small amount of air that remains inside the chip when chip is prepared and the air that may be released under high temperature during the PCR reaction which may be originally dissolved in the oil and aqueous phase, can be temporarily stored. This avoids the repeated agitation of oil and aqueous phase during the PCR process due to repeated expansion and contraction of the forming air bubble when no bubble storage groove may be provided. Repeated agitation can lead to the instability and fusion of droplets, which in turn causes the failure of reactions.

Further, with a long and tortuous injection flow channel, the flow pressure entering the droplet generating channels can be equilibrated, which increases the stability of droplet generation.

These and other features, aspects, and advantages of the present invention will become better understood with regard to the following description, appended claims, and accompanying drawings.

DETAILED DESCRIPTION OF THE INVENTION

The following examples, including the experiments conducted and results achieved are provided for illustrative purpose only and are not to be construed as limiting upon the present invention.

Embodiment 1

As shown in FIGS. 1 to 5, a droplet digital PCR chip includes a chip unit, and the chip unit includes a chip body formed by bonding a top piece 1 and a bottom piece 2. The chip body is internally provided with an inlet chamber 3, a droplet storage chamber 4, and an oil outlet chamber 5.

In the present invention, the internal structures of the chip body include, but is not limited to, an inlet chamber, a droplet storage chamber, and an oil outlet chamber. The internal structures may be disposed on an inner wall of the top piece, or on an inner wall of the bottom piece of the chip, or formed after a bonding of the top and bottom pieces, as long as the top and bottom pieces are bonded together to form a desired microstructure.

Figure 1:
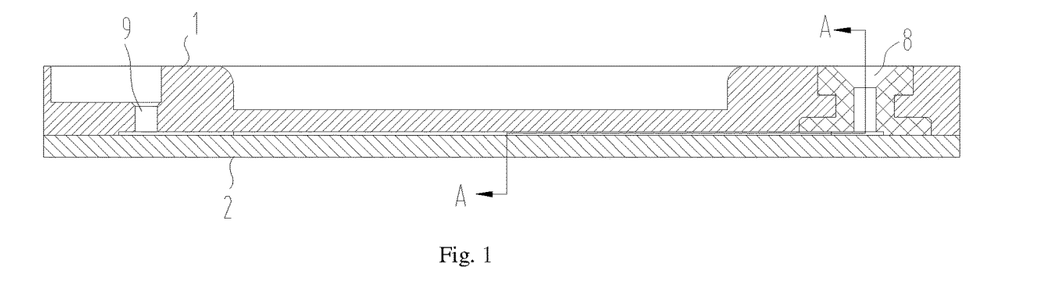
FIG. 1 illustrates a schematic cross-sectional view of a droplet digital PCR chip in embodiment 1.
Figure 2:
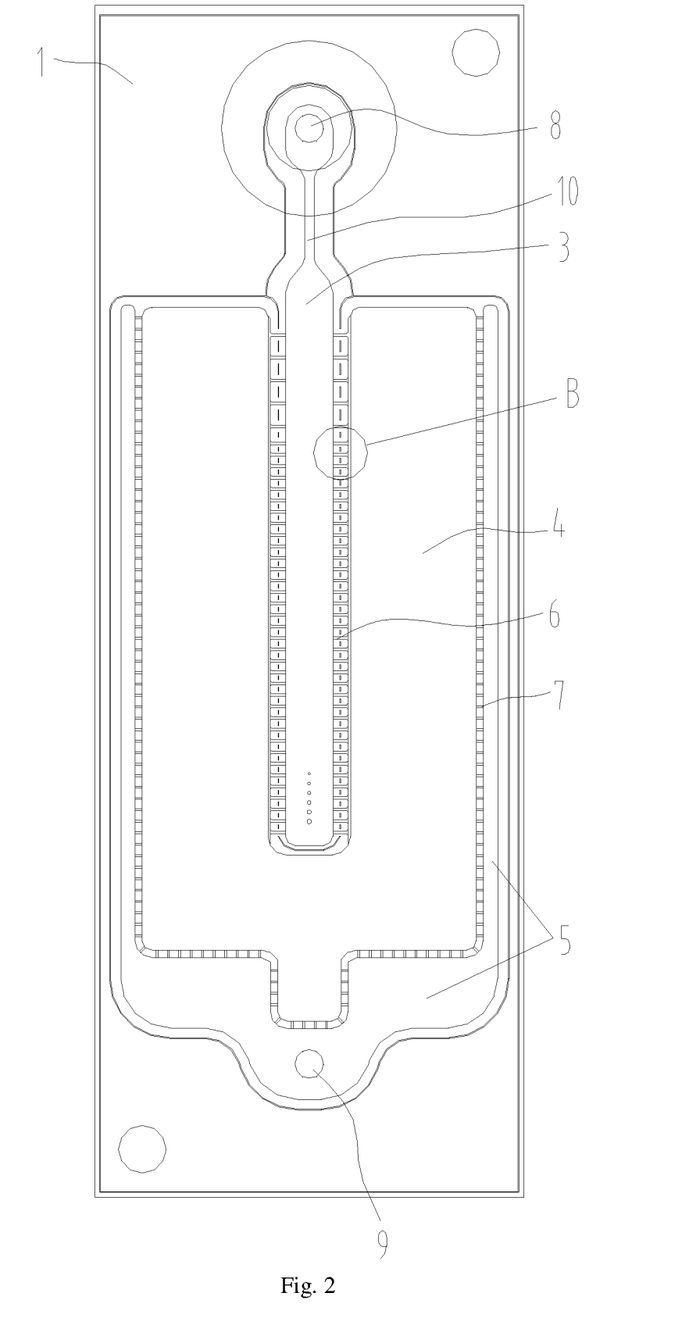
FIG. 2 illustrates a schematic structural view of a top piece on an inner side of the chip.
Figure 3:
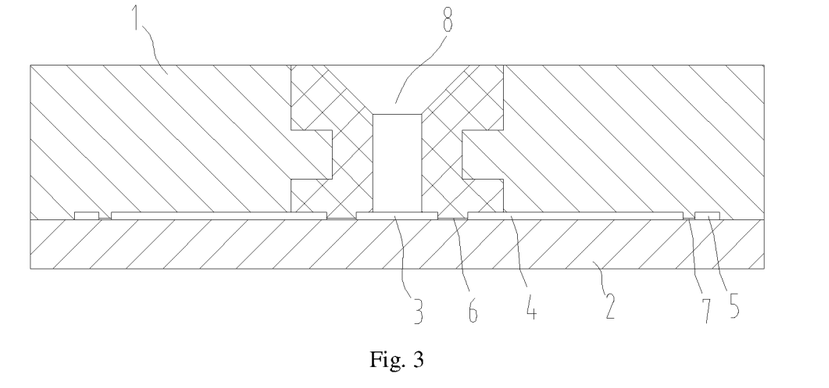
FIG. 3 illustrates a schematic cross-sectional view of the droplet digital PCR chip of FIG. 1 along the A-A direction.

In this embodiment, the microstructure is located on the inner wall of the top piece, that is, a side of the top piece facing the inner wall of the chip.

Specifically, as shown in FIG. 2, the droplet storage chamber 4 is in a U-shaped structure. The inlet chamber 3 is in a linear structure, and is disposed between two arms of the U-shaped structure. A plurality of droplet generating channels 6 are parallelly disposed between the inlet chamber and the two arms. The oil outlet chamber 5 is located on an outer side of the U-shaped structure. A plurality of oil outlet channels 7 are provided between the droplet storage chamber 4 and the oil outlet chamber 5. Heights of the droplet generating channel 6 and the oil outlet channel 7 both are smaller than a height of the droplet storage chamber 4, so that a specific terrace with a function of droplets generation is formed at a junction between the droplet generating channel 6 and the droplet storage chamber 4.

The droplet storage chamber 4 is in a U-shaped structure, so that the elongated inlet chamber 3 extends into an interior of the droplet storage chamber 4. A plurality of droplet generating channels 6 can be disposed on a top of and along two sides of the inlet chamber 3 to increase a speed of droplet generation. Meanwhile, it also makes all boundaries of the droplet storage chamber 4 not too far from the droplet generating channels, avoiding generated droplets migrate over long distances to cause damage and loss.

An injection hole 8 connecting to the inlet chamber 3 and an oil drain hole 9 connecting to the oil outlet chamber 5 both are disposed on a surface of the chip.

An end of the inlet chamber close to the injection hole 8 is defined as an injection end. An elongated connecting channel 10 is disposed between the injection end and the injection hole 8. An arrangement density of the droplet generating channels 6 gradually increases from the injection end to another end of the inlet chamber 3. This arrangement with a gradient density allows the droplets to be generated at a similar rate in different locations. If the droplet generating channels are evenly disposed, a pressure on the droplet generating channels 6 close to the injection hole is larger than those at far side, driving the aqueous phase flowing faster and generating more droplets.

Figure 4:
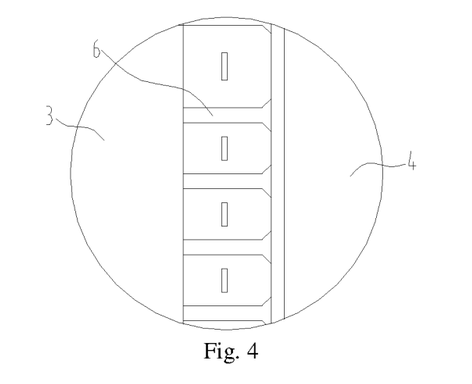
FIG. 4 illustrates a partial enlarged view of area B in FIG. 2.
Figure 5:
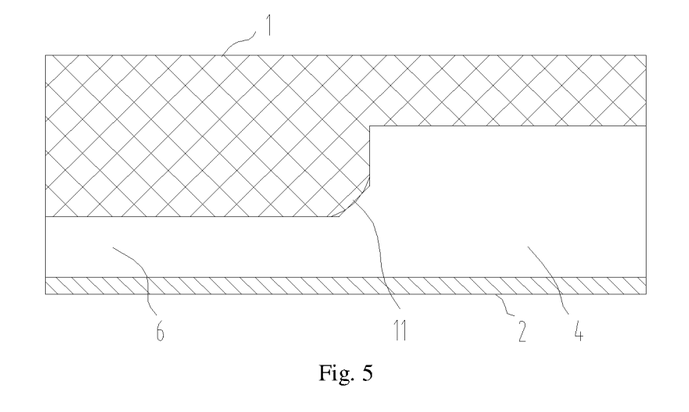
FIG. 5 illustrates a schematic partial structural view of a droplet generating channel and a droplet storage chamber.

An end of the droplet generating channel 6 connecting with the droplet storage chamber 4 is provided with a circular chamfer 11. A length of the circular chamfer 11 in a droplet formation direction is ranging from 1 μm to 500 μm. The length of the circular chamfer 11 in the droplet formation direction affects a size of the generated droplets. Within a certain range, the size of the generated droplets increases as the length increases.

A cross section of the droplet generating channel 6 is rectangular with a width ranging from 10 μm to 500 μm and a height ranging from 1 μm to 400 μm. A depth of droplet storage chamber is ranging from 2 μm to 1000 μm. A width of the droplet generating channel 6 close to the end connecting with the droplet storage chamber 4 becomes larger to form a bell mouth structure. The size of the droplets is directly related to a size of the droplet generating channel 6, which means the larger the inlet channels 6, the larger the droplets. Thus, the size of droplet generating channel 6 needs to be within a reasonable range. A bell mouth structure facilitates the generation and movement of droplets.

The injection hole 8 is sealed by a silicone plug which has a through hole. Due to good elasticity of silicone material, a pipette can be tightly matched with the silicone plug during a loading of oil phase or aqueous phase, which ensures the airtightness of the chip channels to make a stable flow rate and pressure and homogeneous droplets generated.

The chip is also engraved with a series of circles of known size in the inlet chamber 3 as a scale, which can be conveniently used to measure the size of the droplets when inspected under a microscope.

When using, the oil phase is firstly injected into inner chambers of the chip through the injection hole 8. After the chip is filled with the oil phase and all bubbles are expelled from the inner chambers, the aqueous phase is injected into the inlet chamber 3 through the injection hole 8 under a certain pressure. When the aqueous phase enters the droplet storage chamber 4 through the droplet generating channels 6, a terrace is formed at the junction of the droplet generating channel 6 and the droplet storage chamber 4 as the height of droplet generating channel 6 is smaller than the droplet storage chamber 4. When the aqueous phase enters a relatively wide droplet storage chamber 4 from the relatively narrow droplet generating channel 6, the aqueous phase partially enters the droplet storage chamber 4 breaks with the aqueous phase in the droplet generating channel 6 as a flow rate is accelerated by a surface tension, forming droplets. After the generated droplets enter the droplet storage chamber 4, the corresponding volume of the oil phase is drained to the oil outlet chamber 5 through the oil outlet channels 7. The oil phase is eventually drained through the oil outlet hole 9 that connects with the oil outlet chamber 5. A height of the oil outlet channels 7 is smaller than a height of the droplet storage chamber 4, so that the droplets are not easily drained from the oil outlet channel 7. Large number of droplets are finally laid in the droplet storage chamber 4. The water-in-oil droplets exist independently, while outer oil phases are mixed with each other, which is equivalent to the presence of droplets of mutually independent aqueous phases in the oil phase. After the droplets are generated, the chip can be directly put into a thermal cycler for a PCR amplification. After the amplification, the chip can be placed into an analysis instrument for imaging and reading fluorescent signals.

Embodiment 2

Figure 6:
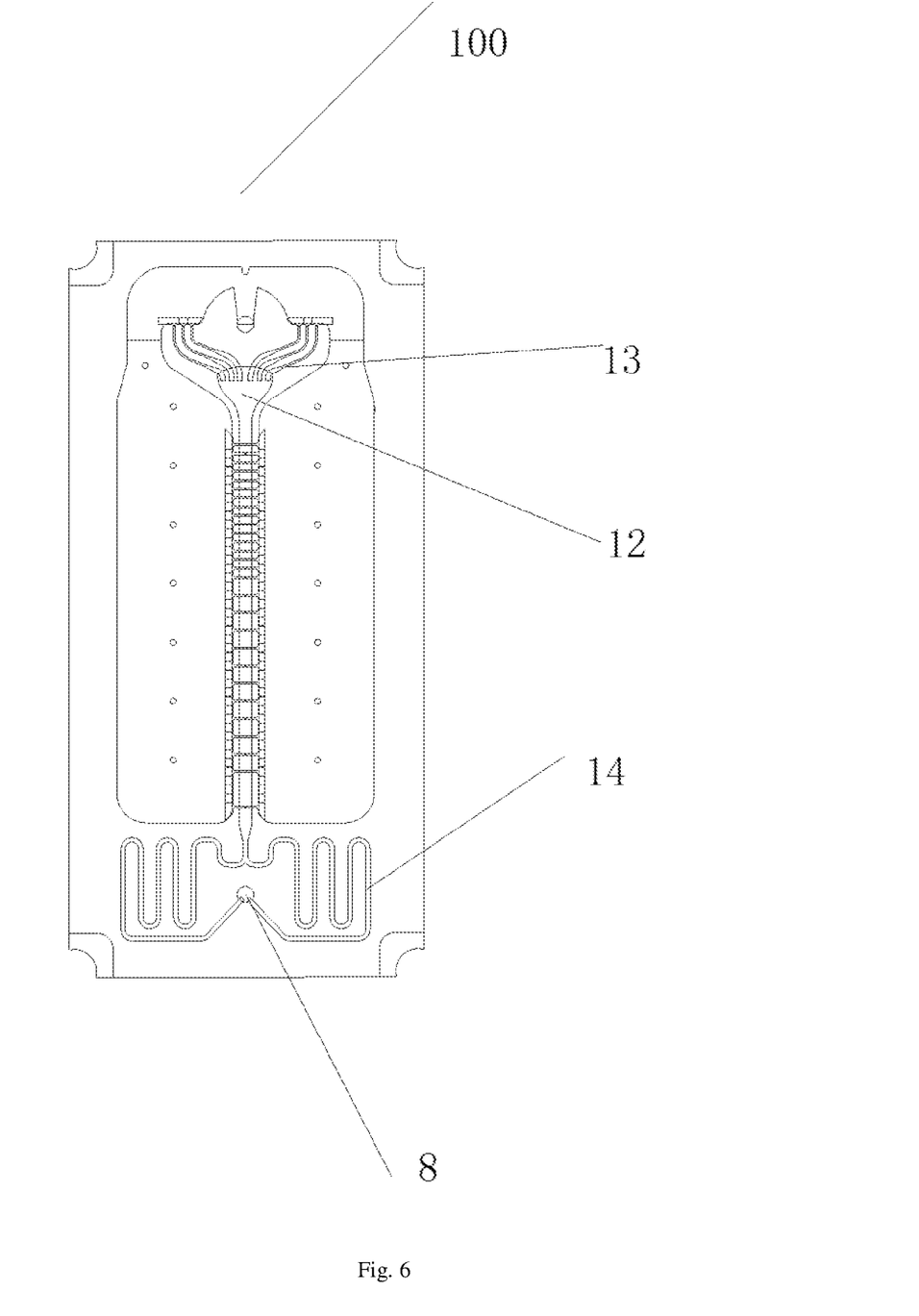
FIG. 6 illustrates a schematic structural view of a droplet digital PCR chip in embodiment 2.

A droplet digital PCR chip includes a chip unit 100. The chip unit 100 also includes a chip body formed by bonding a top piece and a bottom piece, as illustrated in Embodiment 1.

The main difference is that the chip body is provided with an inlet chamber and a droplet storage chamber. However, there is no oil outlet chamber.

Moreover, the chip may further be provided with a bubble storage groove 12. The bubble storage groove 12 is connected to the droplet storage chamber 4 through a plurality of bubble channels 13.

The bubble storage groove 12 is mainly used for storing the bubbles in the droplet storage chamber 4. There is no special requirement for a position and a structure thereof. Considering a layout and rational utilization of the whole chip, the bubble storage groove 12 can be disposed at a corner space of the chip to utilize the corner space as much as possible without occupying the main space of the chip.

In this embodiment, the bubble storage groove 12 and corresponding bubble channels 13 are provided at an end of the inlet channel.

Further comparison with embodiment 1, an injection flow channel 14 is disposed between the injection hole 8 and the inlet chamber 3. The injection flow channel 14 can extend a time of injection fluid flow from the injection hole 8 to the inlet chamber 3, and balance a pressure when the injection fluid enters into the droplet generating channel 6.

The injection flow channel 14 can be in various forms. In order to increase the pressure equilibrium of injection fluid enter into the droplet inlet channel and the stability of the droplets, the injection flow channel 14 can be designed as long and tortuous as possible.

Embodiment 3

Figure 7:
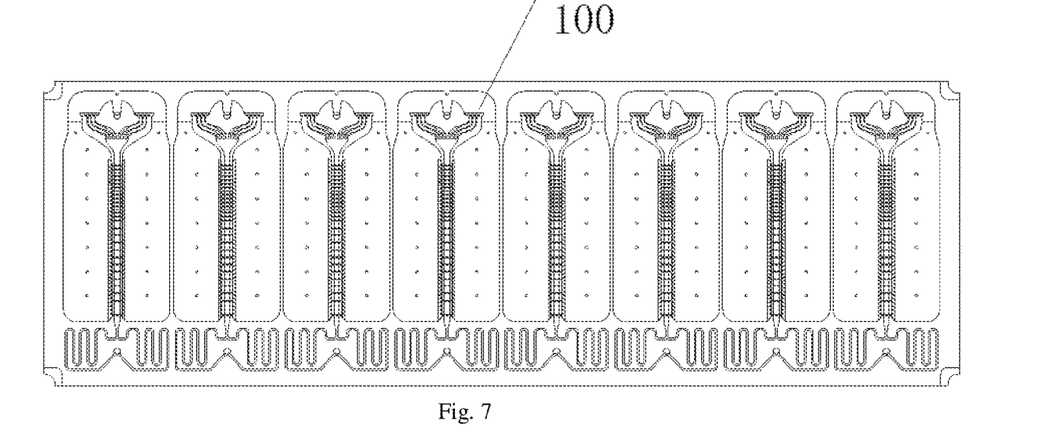
FIG. 7 illustrates a schematic structural view of a droplet digital PCR chip in embodiment 3.

As shown in FIG. 7, a plurality of chip units 100 are disposed on one chip body. The structure of each chip unit 100 is the same as that in Embodiment 2.

Embodiment 4

A plurality of chip units are disposed on one chip body, and the structure of each chip unit is the same as that in Embodiment 1.

Embodiment 5

By using the droplet digital PCR chip in Embodiment 1, and 70% mineral oil+30% Tetradecane+3% EM90+3% Triton X-100 as the oil phase (the ratio of mineral oil and Tetradecane is mass/mass ratio to form the main component of the oil phase, the ratio of EM90 and TritonX-100 is mass/mass ratio to be added additionally to the main component), the droplet generation and PCR amplification are carried out. The process is described in detail as follows:
(1) Preparing the oil phase.
(2) Preparing the aqueous phase, i.e. the PCR reaction mixture.

The template was derived from non-small cell lung cancer (NSCLC) cell line H1975, with both T790M and L858R mutations.

The primer sequences are:

F: 5'-GCCTGCTGGGCATCTG-3'; (SEQ ID NO: 1)

R: 5'-TCTTTGTGTTCCCGGACATAGAC-3'; (SEQ ID NO: 2)

The probe sequence is:
5'- FAM- ATGAGCTGCATGATGAG -MGB-NFQ -3' (SEQ ID NO: 3), wherein FAM is a fluorescent reporter and NFQ is a quencher.

PCR reaction mixture:

| Components | Volume (μl) |
|---|---|
| 2 × PCR buffer(Taq polymerase, dNTP、Mg$^{2+}$ includes) | 7.5 |
| BSA (1%) | 1.5 |
| Primer F (10 μM) | 0.3 |
| Primer R (10 μM) | 0.3 |
| Probe (5 μM) | 0.3 |
| Template (5 ng/μl) | 1.0 |
| Water, nuclease-free | 4.1 |
| Total Volume | 15 |

(3) Filling the droplet digital PCR chip with oil phase.
(4) Generating droplets with the step emulsification method while adding the aqueous phase to the oil phase using a syringe pump.
(5) Performing PCR amplification according to the following procedure:
96° C. for 10 min, and 40 cycles of 30 s at 98° C. and 60 s at 62° C., followed by 62° C. for 60 s, incubate at 25° C.
(6) After amplification, observing the morphology of the droplets under a microscope. If the droplets are homogenous and stable, detect the fluorescent signal with a chip scanner.

Figure 8:
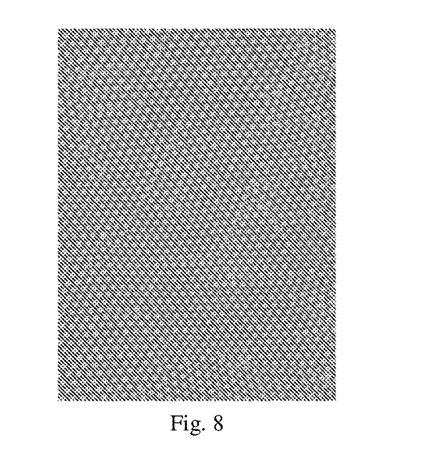
FIG. 8 illustrates a view of generated droplets in embodiment 4.
Figure 9:
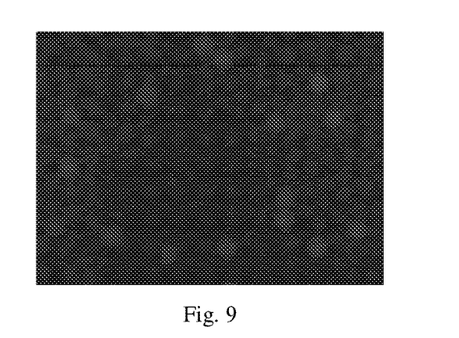
FIG. 9 illustrates droplet fluorescent signals in embodiment 4.

Results: After the PCR amplification, the droplets were homogenous, and the diameter was about 80 μm. There was hardly any broken and fused droplet (FIG. 8), and strong fluorescent signals can be detected by chip scanner (FIG. 9).

Embodiment 6

Figure 10:
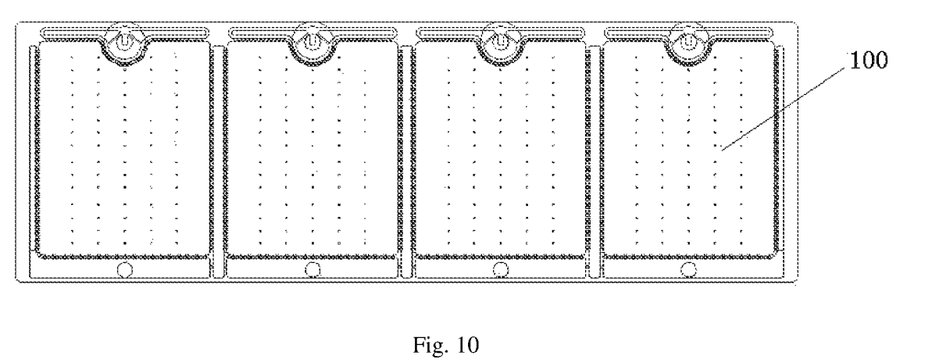
FIG. 10 illustrates a schematic structural view of a droplet digital PCR chip in embodiment 5.
Figure 11:
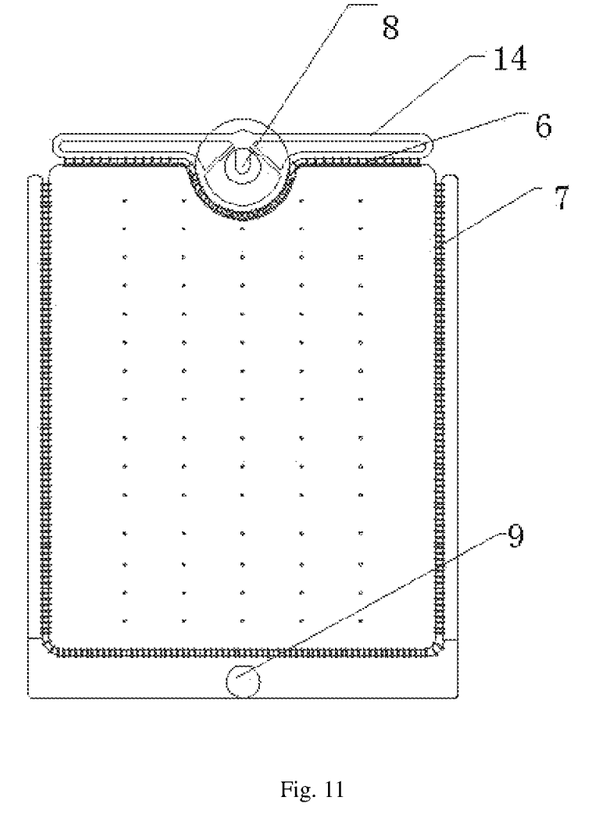
FIG. 11 illustrates a schematic structural view of a chip unit in FIG. 10.

As shown in FIG. 10, a plurality of chip units 100 are disposed on one chip, and the structure of each chip unit 100 is basically identical (FIG. 11). The design principle of the main structure of the chip unit is the same as that in Embodiments 1 and 2. The inlet chamber, the droplet storage chamber and the oil outlet chamber are also provided inside the chip unit.

Different from embodiment 1, an injection flow channel 14 is disposed between the injection hole 8 and the inlet chamber 3 as that in Embodiment 2. The injection flow channel 14 can extend a flowing time of injection fluid from the injection hole 8 to the inlet chamber 3, and balance a pressure when the injection fluid enters into the droplet generating channel 6.

In the present embodiment, the injection flow channel 14 is disposed in a ring shape. An upper half of the annular flow channel stores part of the aqueous phase, so that the lower half, which connects with the droplet generating channel, always maintains a certain amount of pressure from aqueous phase. With such design, the annular flow channel is used to disperse and equilibrate the flow pressure, so that the pressure is evenly released. Meanwhile, the intervals between the droplet generating channels can be adjusted according to the change of the flow pressure, so that the pressure of each droplet generating channel is equilibrated at maximum degree and the droplets are homogenous. Thus, the force on droplets is unidirectional and the droplets move in one direction, which reduces the risk of droplet fusion.

In addition, the oil outlet chamber is disposed in a regular U shape, surrounding the three sides of the droplet storage chamber. The oil outlet channel 7 is evenly disposed between the droplet storage chamber and the oil outlet chamber. This kind of oil outlet channel 7 reduces the oil drain pressure, facilitating the quick drain of the oil phase.

Embodiment 7

Using the droplet digital PCR chip in Embodiment 6, and 70% mineral oil+30% Tetradecane+3% EM90+3% Triton X-100 as the oil phase (the ratio of mineral oil and Tetradecane is mass/mass ratio to form the main component of the oil phase, the ratio of EM90 and TritonX-100 is mass/mass ratio to be added additionally to the main component), the droplet generation and PCR amplification are carried out. The process is described in detail as follows:
(1) Preparing the oil phase.
(2) Preparing the aqueous phase, i.e. the PCR reaction mixture.

The template was derived from non-small cell lung cancer (NSCLC) cell line H1975, with both T790M and L858R mutations.

The primer sequences are:

F: 5'-GCCTGCTGGGCATCTG-3'; (SEQ ID NO: 1)

R: 5'-TCTTTGTGTTCCCGGACATAGAC-3'; (SEQ ID NO: 2)

The probe sequence is:
5'- FAM- ATGAGCTGCATGATGAG -MGB-NFQ -3' (SEQ ID NO: 3), wherein FAM is a fluorescent reporter and NFQ is a quencher.

PCR Mixture:

| Components | Volume (μl) |
|---|---|
| 2 × PCR buffer(Taq polymerase, dNTP ` $Mg^{2+}$ includes) | 7.5 |
| BSA (1%) | 1.5 |
| Primer F (10 μM) | 0.3 |
| Primer R (10 μM) | 0.3 |
| Probe (5 μM) | 0.3 |
| Template (5 ng/μl) | 1.0 |
| Water, nuclease-free | 4.1 |
| Total Volume | 15 |

(3) Filling the droplet digital PCR chip with oil phase.
(4) Generating droplets with the step emulsification method while adding the aqueous phase to the oil phase using a syringe pump.
(5) Performing PCR amplification according to the following procedure:
96° C. for 10 min and 40 cycles of 30 s at 98° C. and 60 s at 62° C., followed by 62° C. for 60 s, incubate at 25° C.
(6) After amplification, observing the morphology of the droplets under a microscope. If the droplets are homogenous and stable, detect the fluorescent signal with a chip scanner.

Results: After the PCR amplification, the droplets were homogenous, and the diameter was about 80-120 μm. There was hardly any broken and fused droplet (FIG. 8), and strong fluorescent signals can be detected by chip scanner.

What is claimed is:
1. A droplet digital PCR chip, comprising:
at least one chip unit, wherein each chip unit comprises a chip body formed by bonding a top piece and a bottom piece and the chip body is internally provided with an inlet chamber,
a droplet storage chamber, and
an injection hole, wherein the injection hole connects with the inlet chamber, a plurality of droplet generating channels are disposed between the inlet chamber and the droplet storage chamber, a height of each of the droplet generating channels is smaller than a height of the droplet storage chamber, an injection fluid is injected into the inlet chamber through the injection hole, and the injection fluid is emulsified and enters the droplet storage chamber at a junction of the droplet generating channels and the droplet storage chamber;
wherein the droplet storage chamber is in a U-shaped structure, the inlet chamber is in a linear structure, the droplet storage chamber is divided into a left arm and a right arm, the left arm and the right arm are disposed on two sides of the chip respectively and the inlet chamber is disposed between the two arms of the U-shaped structure;
wherein a plurality of droplet generating channels are disposed along two sides of the inlet chamber to increase a speed of droplet generation;
wherein the injection hole connecting to the inlet chamber is disposed on a surface of the chip, an end of the inlet chamber close to the injection hole is an injection end, an arrangement density of the droplet generating chan-

SEQUENCE LISTING

<160> NUMBER OF SEQ ID NOS: 3

<210> SEQ ID NO 1
<211> LENGTH: 16
<212> TYPE: DNA
<213> ORGANISM: Artificial Sequence
<220> FEATURE:
<223> OTHER INFORMATION: A synthetic sequence

<400> SEQUENCE: 1
gcctgctggg catctg                                                   16

<210> SEQ ID NO 2
<211> LENGTH: 23
<212> TYPE: DNA
<213> ORGANISM: Artificial Sequence
<220> FEATURE:
<223> OTHER INFORMATION: A synthetic sequence

<400> SEQUENCE: 2
tctttgtgtt cccggacata gac                                           23

<210> SEQ ID NO 3
<211> LENGTH: 17
<212> TYPE: DNA
<213> ORGANISM: Artificial Sequence
<220> FEATURE:
<223> OTHER INFORMATION: A synthetic sequence

<400> SEQUENCE: 3
atgagctgca tgatgag                                                  17 nels gradually increases from the injection end to another end of the inlet chamber.

2. The droplet digital PCR chip according to claim 1, wherein the chip further comprises an oil outlet chamber and an oil outlet hole, and the oil outlet chamber is connected to the droplet storage chamber through a plurality of oil outlet channels.

3. The droplet digital PCR chip according to claim 2, wherein the oil outlet chamber is disposed on an outer side of the droplet storage chamber.

4. The droplet digital PCR chip according to claim 1, wherein the chip is provided with a bubble storage groove, and the bubble storage groove is connected with the droplet storage chamber through at least one bubble channel.

5. The droplet digital PCR chip according to claim 1, wherein an injection flow channel is disposed between the injection hole and the inlet chamber, the injection flow channel extends a flowing time of injection fluid from the injection hole to the inlet chamber, and balances a pressure when the injection fluid enters into the droplet generating channel.

6. The droplet digital PCR chip according to claim 1, wherein a plurality of droplet generating channels are parallelly disposed between the inlet chamber and two arms.

7. The droplet digital PCR chip according to claim 6, wherein the droplet generating channels between the inlet chamber and the droplet storage chamber is disposed according to a pressure changing in the inlet channel, intervals between the droplet generating channels are small at a far end of the inlet chamber from the injection hole, and the intervals increases gradually to a near end of the inlet chamber from the injection hole, so that the pressure in each of the droplet generating channels is basically consistent.

8. The droplet digital PCR chip according to claim 1, wherein a bell mouth structure is formed by increasing a width of an end of the droplet generating channel close to the droplet storage chamber.

9. The droplet digital PCR chip according to claim 1, wherein a circular chamfer is disposed at an end of the droplet generating channel connecting with the droplet storage chamber.

10. The droplet digital PCR chip according to claim 1, wherein an upper surface of the droplet storage chamber is provided with at least one vent hole.

11. The droplet digital PCR chip according to claim 1, wherein a silicone plug is disposed at an inlet of the injection hole, and the silicone plug is provided with a through hole to connect with the inlet chamber.

12. The droplet digital PCR chip according to claim 1, wherein droplets are laid in a single, a double, or a multi-layer array in the droplet storage chamber of the chip, and the droplets remain stable after a reaction or a detection.

13. The droplet digital PCR chip according to claim 1, wherein the chip comprises a plurality of chip units, and the chip units are parallelly arranged.

* * * * *